United States Patent [19]

Reuschling et al.

[11] Patent Number: 4,804,755

[45] Date of Patent: Feb. 14, 1989

[54] PROCESS FOR THE PREPARATION OF 6-METHYL-3,4-DIHYDRO-1,2,3-OXATHIAZIN-4-ONE 2,2-DIOXIDE AND FOR THE PURIFICATION THEREOF

[75] Inventors: Dieter Reuschling, Butzbach; Adolf Linkies, Frankfurt am Main; Walter Reimann, Hofheim am Taunus; Otto E. Schweikert, Kelkheim; Karl E. Mack, Wiesbaden; Wolfgang Ebertz, Hattersheim am Main, all of Fed. Rep. of Germany

[73] Assignee: Hoechst Aktiengesellschaft, Frankfurt, Fed. Rep. of Germany

[21] Appl. No.: 902,427

[22] Filed: Aug. 29, 1986

[30] Foreign Application Priority Data

Sep. 3, 1985 [DE] Fed. Rep. of Germany ....... 3531358

[51] Int. Cl.[4] ............................................ C07D 291/06
[52] U.S. Cl. ...................................................... 544/2
[58] Field of Search ........................................... 544/2

[56] References Cited

U.S. PATENT DOCUMENTS 4,638,063 1/1987 Clauss et al. ............................ 544/2

FOREIGN PATENT DOCUMENTS 2453063 5/1976 Fed. Rep. of Germany .......... 544/2

OTHER PUBLICATIONS

Clauss et al., Angewandte Chemie, Intl. Ed., 12, 869–876 (1973) ("Oxathiazinone Dioxides . . . ").
Petersen, Ber., 83, 551–558 (1950) ("Concerning New Reactions of Sulfamides").

Primary Examiner—John M. Ford
Attorney, Agent, or Firm—Connolly & Hutz

[57] ABSTRACT

The non-toxic salts of 6-methyl-3,4-dihydro-1,2,3-oxothiazin-4-one 2,2-dioxide are prepared by cyclizing acetoacetamide-N-sulfonic acid or its salts with an at least approximately equimolar amount of SO3 in the presence of a water-immiscible, inert organic solvent and, if appropriate, also an inert inorganic solvent, hydrolyzing the 6-methyl-3,4-dihydro-1,2,3-oxathiazin-4-one 2,2-dioxide obtained in the form of the SO3-adduct after the cyclization reaction, in the event that the amount of SO3 employed is more than equimolar, purifying the organic phase (which has separated out) by extraction with a small volume of water or dilute aqueous sulfuric acid, preferably only with water, and isolating, by neutralization with bases, the non-toxic salts of the 6-methyl-3,4-dihydro-1,2,3-oxathiazin-4-one 2,2-dioxide from the organic phase thus purified.

The said salts are obtained in this process in an extremely pure form; they are valuable synthetic sweetening agents. The potassium salt is known as acesulfam (K).

14 Claims, No Drawings

PROCESS FOR THE PREPARATION OF 6-METHYL-3,4-DIHYDRO-1,2,3-OXATHIAZIN-4-ONE 2,2-DIOXIDE AND FOR THE PURIFICATION THEREOF

6-Methyl-3,4-dihydro-1,2,3-oxathiazin-4-one 2,2-dioxide is the compound of the formula

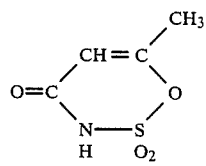

As a result of the acid hydrogen on the nitrogen atom, the compound is capable of forming salts (with bases). The non-toxic salts—such as, for example, the Na, K and Ca salt—can be used as sweetening agents in the food industry because of their sweet taste, in some cases intense sweet taste, the K salt ("Acesulfam K" or just "Acesulfam") being of particular importance.

A number of different processes are known for the preparation of 6-methyl-3,4-dihydro-1,2,3-oxathiazin-4-one 2,2-dioxide and its non-toxic salts; cf. Angewandte Chemie 85, issue 22 (1973), pages 965 to 973, corresponding to International Edition Volume 12, No. 11 (1973), pages 869–76. Virtually all the processes start from chlorosulfonyl or fluorosulfonyl isocyanate ($XSO_2NCO$ in which $X=Cl$ or $F$). The chlorosulfonyl or fluorosulfonyl isocyanate is then reacted with monomethylacetylene, acetone, acetoacetic acid, tert.-butyl acetoacetate or benzyl propenyl ether (in a multi-stage reaction in most cases) to give acetoacetamide-N-sulfochloride or acetoacetamide-N-sulfofluoride, which cyclizes under the influence of bases (such as, for example, methanolic KOH) and affords the corresponding salts of 6-methyl-3,4-dihydro-1,2,3-oxathiazin-4-one 2,2-dioxide. The free oxathiazinone can, if desired, be obtained from the salts in a customary manner (by means of acids).

A further process for the preparation of the oxathiazinone intermediate stage acetoacetamide N-sulfofluoride starts from sulfamoyl fluoride $H_2NSO_2F$, the partial hydrolysis product of fluorosulfonyl isocyanate (German Offenlegungsschrift No. 2,453,063). The fluoride of sulfamic acid $H_2NSO_2F$ is then reacted with an approximately equimolar amount of the acetoacetylating agent diketene in an inert organic solvent in the presence of an amine at temperatures between about $-30°$ and $100°$ C.; the reaction proceeds in accordance with the following equation (using triethylamine as the amine):

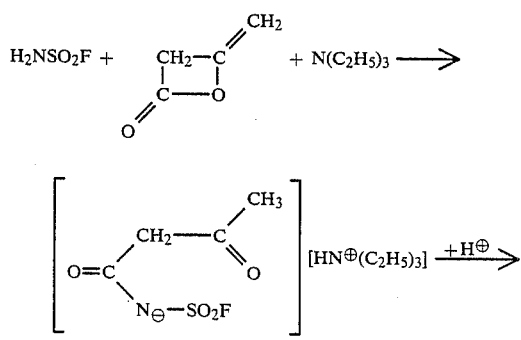

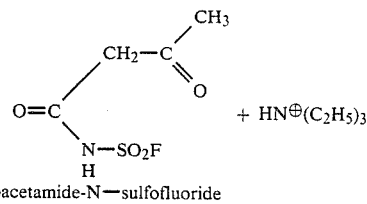

Acetoacetamide-N-sulfofluoride

The acetoacetamide-N-sulfofluoride is then cyclized to give the sweetening agent in a customary manner by means of a base, for example methanolic KOH:

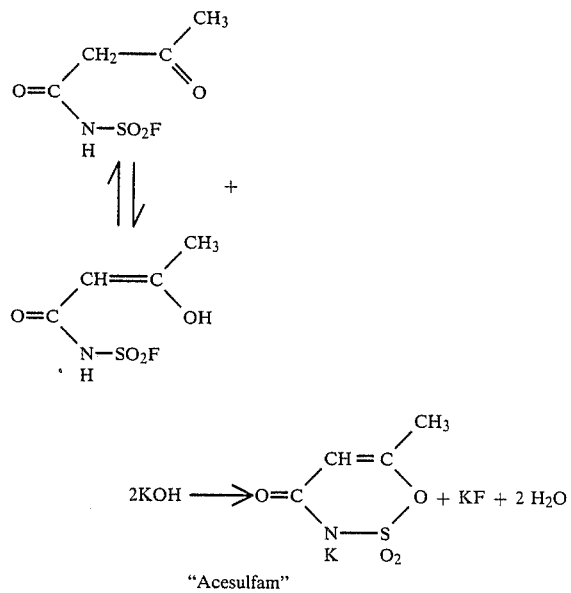

"Acesulfam"

Although the known processes give yields of 6-methyl-3,4-dihydro-1,2,3-oxathiazin-4-one 2,2-dioxide and its non-toxic salts which are in some cases quite satisfactory (up to approx. 85% of theory, relative to the sulfamoyl halide starting materials), they are still in need of improvement, particularly for industrial purposes, because of the need to employ the starting materials chlorosulfonyl or fluorosulfonyl isocyanate, which are not very easily accessible; this is because, owing to the starting materials (HCN, $Cl_2$, $SO_3$ and HF), some of which are rather unpleasant to handle, the preparation of chlorosulfonyl and fluorosulfonyl isocyanate requires considerable precautionary measures and safety precautions. The preparation of chlorosulfonyl and fluorosulfonyl isocyanate is based on the following equations:

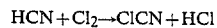

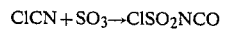

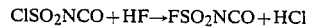

The replacement of sulfamoyl fluoride in the process according to German Offenlegungsschrift No. 2,453,063 mentioned above, for instance by sulfamic acid $H_2NSO_3H$ or salts thereof, which is considerably easier to obtain (for example from $NH_3+SO_3$), hardly seemed promising for the simple reason that the reaction of Na sulfamate $H_2NSO_3Na$ with diketene in an aqueous alkaline solution does not give any reaction product which can be isolated in a pure state. On the contrary, it has only been possible to isolate the 1:1-adduct which is formed in this reaction, probably at least together with other products, in the form of the coupling products with 4-nitrophenyldiazonium chloride as a pale yellow dyestuff; cf. Ber. 83 (1950), pages 551–558, in particular page 555, last paragraph before the description of the experiments and page 558, last paragraph:

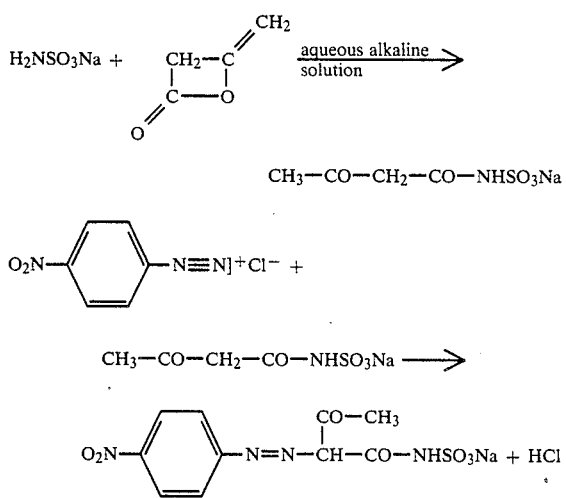

Moreover, acetoacetamide-N-sulfonic acid has otherwise been postulated only, or also, as an intermediate product in the decomposition of 6-methyl-3,4-dihydro-1,2,3-oxathiazine-4-one 2,2-dioxide when the latter is boiled in aqueous solution; cf. the literature quoted initially, Angew. Chemie (1973) (loc. cit.):

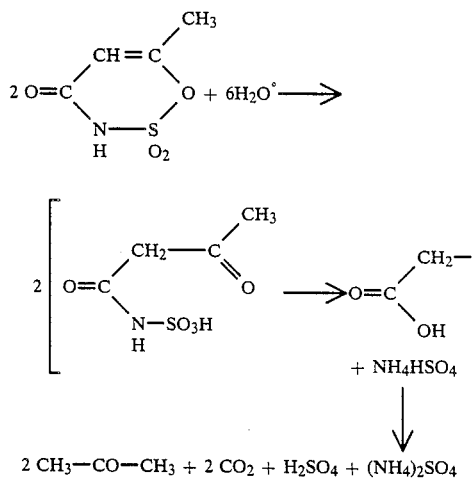

Because the processes of the state of the art for the preparation of 6-methyl-3,4-dihydro-1,2,3-oxathiazin-4-one 2,2-dioxide and its non-toxic salts are not entirely satisfactory, above all for being carried out on an industrial scale, in particular as a result of the need to employ starting materials which are not readily accessible, it was, therefore, required to improve the known processes appropriately or to develop a new, improved process.

In order to achieve this object, it has already been suggested that the process according to German Offenlegungsschrift No. 2,453,063 should be modified chiefly by replacing the sulfamoyl fluoride in the known process by salts of sulfamic acid and by subsequently cyclizing the resulting acetoacetylation product by means of SO₃ (European Patent Application No. 85,102,885.2—Publication Number 0,155,634—with the priority of German Application No. P 3,410,439.9 dated 22.3.1984—HOE 84/F 064).

The patent application last mentioned relates particularly to a process for the preparation of 6-methyl-3,4-dihydro-1,2,3-oxathiazin-4-one 2,2-dioxide and its non-toxic salts by (a) reacting a sulfamic acid derivative with an at least approximately equimolar amount of an acetoacetylating agent in an inert organic solvent, if appropriate in the presence of an amine or phosphine catalyst, to give an acetoacetamide derivative and (b) cyclizing the acetoacetamide derivative; the process comprises using, as the sulfamic acid derivative in stage (a), a salt of sulfamic acid which is at least partly soluble in the inert organic solvent employed, cyclizing the acetoacetamide-N-sulfonate formed in this stage or the free acetoacetamide-N-sulfonic acid in stage (b) by the action of an at least approximately equimolar amount of SO₃, if appropriate in an inert inorganic or organic solvent, to give 6-methyl-3,4-dihydro-1,2,3-oxa-thiazin-4-one 2,2-dioxide, and then, if desired, also neutralizing with a base, in a stage (c), the product obtained here in the acid form.

The following are indicated in the abovementioned patent application (using diketene as the acetoacetylating agent) as the reactions on which the process is based:

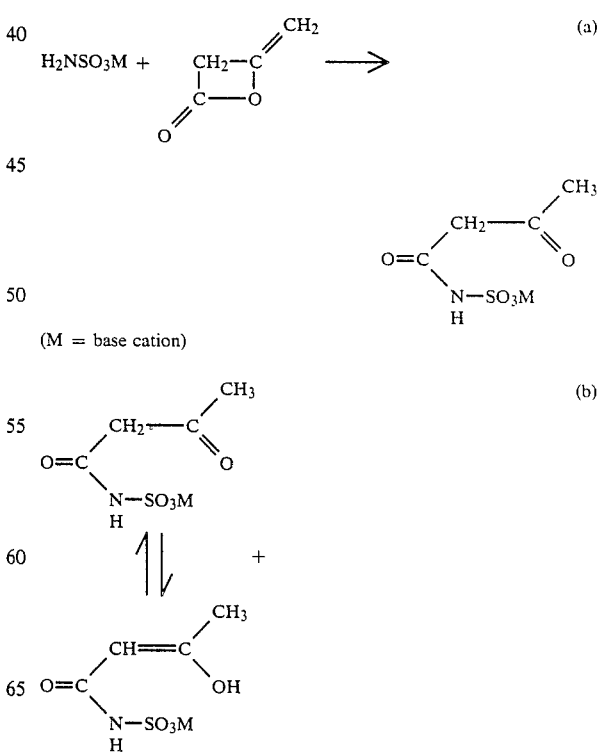

-continued

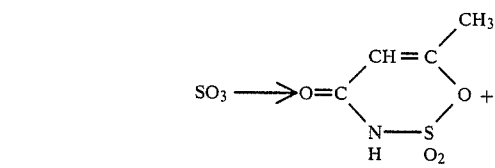

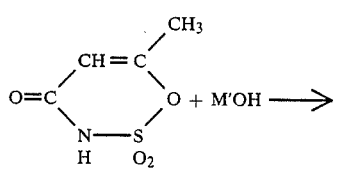

(M' = base cation)

Stage (b) in this scheme of reactions is shown with an amount of $SO_3$ which is equimolar in respect of the acetoacetamide-N-sulfonate. It is preferable, however, to use an excess of $SO_3$. An intermediate product is then formed, the chemical structure of which is not yet accurately known, but which possibly constitutes an $SO_3$ adduct of 6-methyl-3,4-dihydro-1,2,3-oxathiazin-4-one 2,2-dioxide—described below as the "$SO_3$-adduct"——and this adduct must then also be hydrolyzed. In this case the abovementioned reaction stage (b) thus comprises 2 partial stages, anmely:

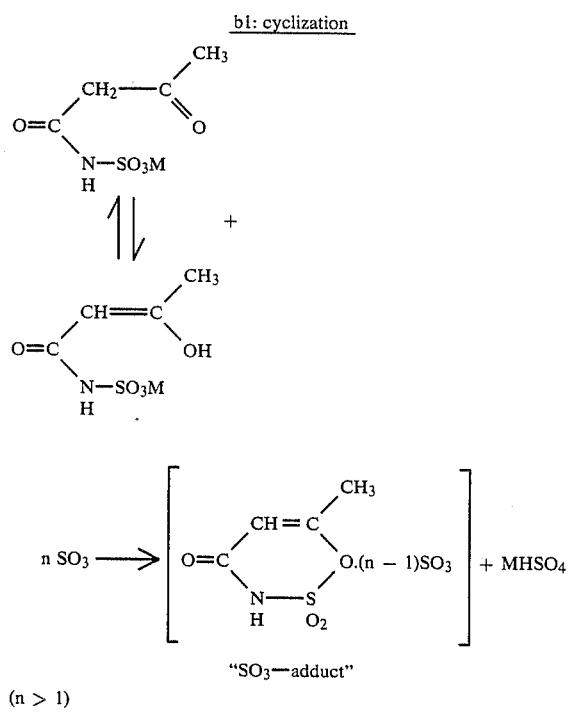

-continued

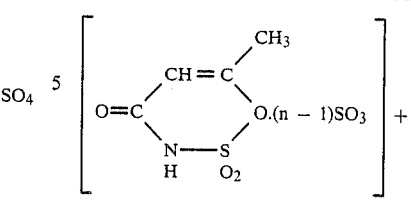

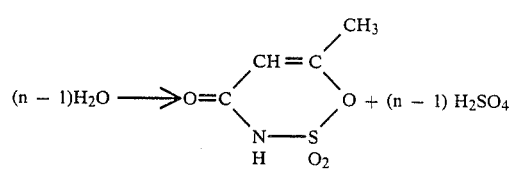

The cyclization reaction (b1) is carried out in accordance with the abovementioned patent application at temperatures between about $-70°$ and $+175°$ C., preferably between about $-40°$ and $+10°$ C.; the reaction times are between about 1 and 10 hours.

The hydrolysis (b2) is carried out after the cyclization reaction by adding water or ice.

Working up is then carried out in a customary manner; working up is, however, only illustrated in detail for the preferred case in which methylene chloride is used as a reaction medium. 2 phases are formed after the hydrolysis in this case, the 6-methyl-3,4-dihydro-1,2,3-oxathiazin-4-one 2,2-dioxide passing mainly into the organic phase. The fractions still present in the aqueous sulfuric acid can be obtained by extraction with a (water-immiscible) organic solvent, such as, for example, methylene chloride or an organic ester.

Alternatively, after water has been added, the reaction solvent is removed by distillation and the 6-methyl-3,4-dihydro-1,2,3-oxathiazin-4-one 2,2-dioxide remaining in the sulfuric acid of the reaction is extracted with a more suitable organic solvent.

The combined organic phases are dried, for example with $Na_2SO_4$, and are concentrated. Sulfuric acid which may have been carried over in the extraction can be removed by the controlled addition of an aqueous alkali solution to the organic phase. If it is intended to isolate the 6-methyl-3,4-dihydro-1,2,3-oxathiazin-4-one 2,2-dioxide, it is advisable also to purify it in a customary manner (preferably by recrystallization). The yield is between about 70 and 95% of theory, relative to the acetoacetamide-N-sulfonate (or the free acid).

If, however, it is intended to isolate a non-toxic salt of 6-methyl-3,4-dihydro-1,2,3-oxathiazin-4-one 2,2-dioxide, the neutralization stage (c) is also carried out. This is effected by neutralizing, in a customary manner, by means of an appropriate base the oxathiazinone compound obtained in the acid form in stage (b). This is carried out, for example, by neutralizing, by means of an appropriate base—preferably a potassium base, such as, for example, KOH, $KHCO_3$, $K_2CO_3$, K alcoholates etc.—the combined, dried and concentrated organic phases at the end of stage (b) in suitable organic solvents, such as, for example, alcohols, ketones, esters or ethers or even water. Or the oxathiazinone compound is neutralized by direct extraction with an aqueous potassium base from the purified organic extraction phase (stage b). The oxathiazinone salt is then precipitated, if necessary after concentrating the solution, in a crystalline form, and can also be purified by recrystallization.

The neutralization stage takes place in a virtually 100% yield.

Reference should be made to the detailed description in the patent application mentioned in regard to the further details of the process.

The process starts from readily accessible and cheap starting materials and is extremely simple to carry out. The yields of the whole process are between about 65 and 95% of theory, relative to the sulfamate starting material.

In the course of further work on this process it has also been suggested that both the cyclization reaction (b1) and the hydrolysis (b2) should be carried out within short to very short times (approx. 10 minutes down to the region of seconds and fractions of a second) (Patent Application No. P 3,527,070.5 dated 29.7.1985—HOE 85/F 134). The practical realization of the process is preferably effected in devices which are suitable and known for carrying out reactions of this type which proceed rapidly and with the evolution of heat (thin film reactors, falling film reactors, spray reactors, tubular reactors with and without internal fitments, etc.). The reaction mixture is worked up as described in the patent application mentioned above. This "short time variant" enables the technical procedure and, in particular, the space-time yield of the process to be considerably improved.

Finally, it has also already been suggested that, instead of stages (a) and (b) of the process of the abovementioned European Patent Application No. 85,102,885.2, acetoacetamide should be reacted with an at least about twice-molar amount of SO₃, if appropriate in an inert inorganic or organic solvent (German Patent Application No. P 3,410,440.2 dated 22.3.1984—HOE 84/F 065). In this case acetoacetamide-N-sulfonic acid is probably first formed in one stage from one mole of acetoacetamide and one mole of SO₃, and then undergoes cyclization with a further mole of SO₃ to give 6-methyl-3,4-dihydro-1,2,3-oxathiazin-4-one 2,2-dioxide in accordance with the following scheme of reactions:

CH₃—CO—CH₂—CONH₂ + SO₃ ——>

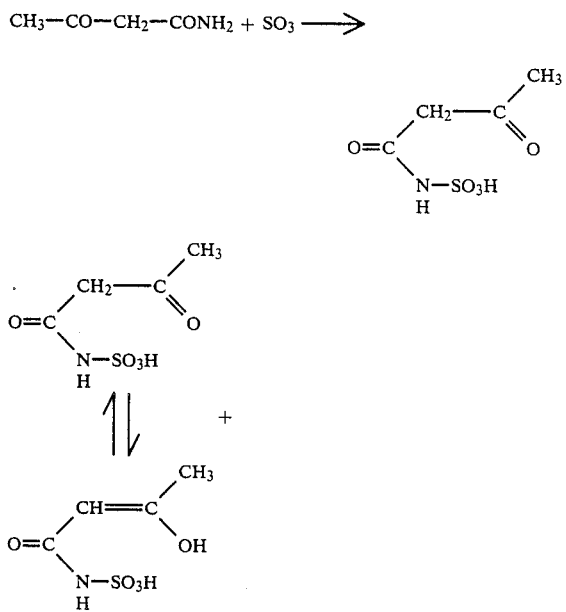

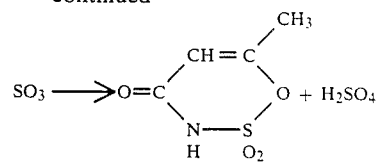

Here too the "SO₃ adduct" is formed with excess SO₃ and must also be hydrolyzed in order to liberate the 6-methyl-3,4-dihydro-1,2,3-oxathiazin-4-one 2,2-dioxide. The working up of the hydrolyzed mixture and, if desired, the conversion of the 6-methyl-3,4-dihydro-1,2,3-oxathiazin-4-one 2,2-dioxide into its non-toxic salts are effected, in principle, in the same way as that described in the abovementioned European Patent Application No. 85,102,885.2. The yield figures for 6-methyl-3,4-dihydro-1,2,3-oxathiazin-4-one 2,2-dioxide are between about 30 and 90% of theory, relative to the acetoacetamide starting material. In all three of the abovementioned patent applications the 6-methyl-3,4-dihydro-1,2,3-oxathiazin-4-one 2,2-dioxide which has been liberated in the hydrolysis of the "SO₃-adduct" is obtained from the organic phase which is formed, after adding water, when using a (water-immiscible) organic solvent for the reaction and/or which is formed if the reaction sulfuric acid is extracted with organic solvents. However, the 6-methyl-3,4-dihydro-1,2,3-oxathiazin-4-one 2,2-dioxide thus obtained and also the non-toxic salts optionally obtained therefrom by reaction with appropriate bases are not always of the required purity, so that various purification operations—preferably recrystallization(s) are often also necessary—involving additional outlay and also associated with loss of substance.

In developing the abovementioned processes further, it has now been found that a considerably purer 6-methyl-3,4-dihydro-1,2,3-oxathiazin-4-one 2,2-dioxide is obtained if it is isolated, not—as described above—from the organic phase, but from the aqueous sulfuric acid phase in a direct manner by crystallization.

The invention relates to a process for the preparation of 6-methyl-3,4-dihydro-1,2,3-oxathiazin-4-one 2,2-dioxide by cyclizing an acetoacetamide derivative; the process comprises using acetoacetamide-N-sulfonic acid or its salts—dissolved in a water-immiscible, inert organic solvent—as the acetoacetamide derivative, carrying out the cyclization by treatment with an at least approximately equimolar amount of SO₃—if appropriate dissolved similarly in a water-immiscible, inert organic solvent or in an inert inorganic solvent—adding aqueous sulfuric acid when the cyclization reaction is complete if an equimolar amount of SO₃ has been employed or—in the event that a more than equimolar amount of SO₃ has been employed, hydrolyzing the 6-methyl-3,4-dihydro-1,2,3-oxathiazin-4-one 2,2-dioxide obtained as the SO₃-adduct after the cyclization reaction, and removing the inert organic solvent from the resulting multi-phase mixture by distillation, and isolating the 6-methyl-3,4-dihydro-1,2,3-oxathiazin-4-one 2,2-dioxide from the residual aqueous sulfuric acid phase by crystallization.

The smooth success of the cyclization of acetoacetamide-N-sulfonic acid and its salts with SO₃ is very surprising, because the elimination of water or bases which takes place with cyclization is not successful, or is in any case not successful for practical purposes, as is known, with other agents for eliminating water or bases, such as, for example, P₂O₅, acetic anhydride, trifluoroacetic anhydride, thionyl chloride etc., as it has already been possible to show in the abovementioned European Patent Application No. 85,102,885.2 by means of a comparison example (using P₂O₅).

Additionally, it is surprising that, when the 6-methyl-3,4-dihydro-1,2,3-oxathiazin-4-one 2,2-dioxide crystallizes from sulfuric acid, a product is obtained which, apart from small amounts of adhering sulfuric acid (which can, however, easily be removed), contains virtually no impurities—at all events virtually no impurities of an organic nature—since it would have been entirely possible to expect that possible dissolved organic impurities—originating from the previous reaction—would crystallize out together with the 6-methyl-3,4-dihydro-1,2,3-oxathiazin-4-one 2,2-dioxide.

The preparation of the acetoacetamide-N-sulfonic acid starting material and its salts is preferably effected by stage (a) of the process of the abovementioned European Patent Application No. 85,102,885.2 by reacting the Li or ammonium salts of sulfamic acid with diketene in inert organic solvents. Solutions of the Li and ammonium salts of acetoacetamide-N-sulfonic acid which can be employed as such without further treatment for the cyclization reaction with SO₃ are obtained in this process.

The possible method, mentioned in European Application No. 85,102,885.2, for obtaining the oxathiazinone compound from the purified organic extraction phase by extractive neutralization with an aqueous potassium base is illustrated in greater detail in that text, in particular in Example 11. In that text, the organic extraction phase is purified by using aqueous alkali solution in order to neutralize sulfuric acid which has been carried over.

In developing the abovementioned processes further, it has now been found that purer salts of 6-methyl-3,4-dihydro-1,2,3-oxathiazin-4-one 2,2-dioxid are obtained in all cases if the organic phase—obtained as described above, is purified, before being worked up further, by extraction with a fairly small volume of water or dilute aqueous sulfuric acid, water being preferred.

The invention relates, therefore, to a process for the preparation of the non-toxic salts of 6-methyl-3,4-dihydro-1,2,3-oxathiazin-4-one 2,2-dioxide by cyclizing an acetoacetamide derivative and neutralizing the product with bases; the process comprises using acetoacetamide-N-sulfonic acid or its salts—dissolved in a water-immiscible, inert organic solvent—as the acetoacetamide derivative, effecting the cyclization by treatment with an at least approximately equimolar amount of SO₃, if appropriate similarly dissolved in a water-immiscible, inert organic solvent or in an inert inorganic solvent, hydrolyzing the 6-methyl-3,4-dihydro-1,2,3-oxathiazin-4-one 2,2-dioxide obtained in the form of the SO₃-adduct after the cyclization reaction, in the event that the amount of SO₃ employed is more than equimolar, purifying the organic phase which is present, or which separates out in the hydrolysis, by extraction with a fairly small volume of water or dilute aqueous sulfuric acid—preferably only with water—and isolating, by neutralization with bases, the non-toxic salts of the 6-methyl-3,4-dihydro-1,2,3-oxathiazin-4-one 2,2-dioxide from the organic phase thus purified.

The smooth success of the cyclization of acetoacetamide-N-sulfonic acid and its salts by means of SO₃ is very surprising, because the elimination of water or bases which takes place in the course of cyclization, that is to say using other agents which eliminate water or bases, such as, for example, P₂O₅, acetic anhydride, trifluoroacetic anhydride, thionyl chloride etc., is not successful, or at all events is not successful for practical purposes, as it has already been possible to show in the abovementioned European Patent Application No. 85,102,885.2 by means of a comparison example (using P₂O₅).

Additionally, it is surprising that the salts of 6-methyl-3,4-dihydro-1,2,3-oxathiazin-4-one 2,2-dioxide obtained in accordance with the process are obtained in an extremely pure form (degree of purity in all cases over 99%), because it would by no means have been automatically expected that virtually all the troublesome impurities would be removed by a simple extraction of the organic phase with water or with dilute aqueous sulfuric acid.

The preparation of the acetoacetamide-N-sulfonic acid starting material and its salts is preferably effected in accordance with stage (a) of the process of the abovementioned European Patent Application No. 85,102,885.2 by reacting the Li or ammonium salts of sulfamic acid with diketene in inert organic solvents. Solutions of the Li and ammonium salts of acetoacetamide-N-sulfonic acid which can be employed as such, without further treatment, for the cyclization reaction with SO₃ are obtained in this process.

It is, of course, also possible to use other salts of acetoacetamide-N-sulfonic acid—in particular alkali and alkaline earth metal salts—for the said cyclization reaction. Compared with the salts, the use of free acetoacetamide-N-sulfonic acid hardly affords any advantages.

As in the case of the salts, the free acetoacetamide-N-sulfonic acid can also be employed immediately for the cyclization reaction in the appropriate solution such as is obtained in the preparation. The solution of free acetoacetamide-N-sulfonic acid which is probably formed as an intermediate in the process of German Patent Application No. P 3,410,440.2 (HOE 84/F 065) can also be regarded as a solution such as is obtained in the preparation.

Inert organic solvents which are suitable for acetoacetamide-N-sulfonic acid or its salts are preferably those from the series of inert organic solvents listed in the abovementioned patent applications which are not miscible with water; i.e. halogenated aliphatic hydrocarbons, preferably having up to 4 carbon atoms, such as, for example, methylene chloride, chloroform, 1,2-dichloroethane, trichloroethylene, tetrachloroethylene, trichlorofluoroethylene etc.; carbonic acid esters of lower aliphatic alcohols, preferably methanol or ethanol; nitroalkanes, preferably having up to 4 carbon atoms and especially nitromethane; and alkyl-substituted pyridines, preferably collidine etc.

The organic solvents can be employed either on their own or as a mixture.

Solvents which are particularly preferred are halogenated aliphatic hydrocarbons, especially methylene chloride.

The concentration of the acetoacetamide-N-sulfonic acids or of its salts in the inert solvent is not critical, but is limited on the one hand by the solubility and, on the other hand by considerations of economy, since at high dilution a great deal of solvent has afterwards to be separated off and worked up once more. In general, concentrations between about 0.1 and 2 mole of acetoacetamide-N-sulfonic acid or its salts per liter are appropriate.

The $SO_3$ can be added either in solid or liquid form or by condensing in $SO_3$ vapor. However, it is preferably added in a dissolved form, in particular dissolved in a water-immiscible, inert organic solvent or in an inert inorganic solvent.

Suitable water-immiscible, inert organic solvents are, in principle, the same solvents as those also used for dissolving the acetoacetamide-N-sulfonic acid or its salts.

Examples of inert inorganic solvents which can be employed are concentrated sulfuric acid or liquid $SO_2$. In principle, the amount of inert solvent employed for the $SO_3$ is not critical either. If a solvent is employed, it is merely necessary to ensure that the $SO_3$ is adequately dissolved; an upper limit is set to the amount of solvent by considerations of economy.

Advantageous concentrations are about 5 to 50% by weight, preferably about 15 to 30% by weight, of $SO_3$.

In a preferred embodiment of the invention, the same inert solvent, preferably belonging to the group of halogenated aliphatic hydrocarbons and especially only methylene chloride, is used both for the acetoacetamide-N-sulfonic acid or its salts and for the $SO_3$.

Although the molar ratio of acetoacetamide-N-sulfonic acid or acetoacetamide-N-sulfonates to $SO_3$ can be about 1:1, an excess of $SO_3$ of up to about 20-fold, preferably a molar excess of about 3-fold to 10-fold and especially about 4-fold to 7-fold, is preferred.

In principle, the cyclization is in other respects carried out in the same manner and under the same conditions as that described in the 3 abovementioned patent applications.

If the acetoacetamide-N-sulfonic acid or its salts and the $SO_3$ are employed in an equimolar amount, no "$SO_3$-adduct" is formed—as can be seen from the reaction schemes displayed initially. Hydrolysis is therefore not necessary in this case.

In the event that the starting compounds—dissolved in inert organic solvents—are employed, the reaction mixture then constitutes the organic phase, and this can, without further separating operations or, if necessary, after the removal of precipitated salts, immediately be recycled for further processing in accordance with the invention.

If the $SO_3$ starting material employed is dissolved in an inert inorganic solvent, such as, for example, concentrated sulfuric acid, the organic phase must be separated off appropriately when the cyclization reaction is complete.

In the preferred case where acetoacetamid-N-sulfonic acid or its salts and $SO_3$ are employed in a molar ratio of 1 to more than 1, an "$SO_3$-adduct" from which the 6-methyl-3,4-dihydro-1,2,3-oxathiazin-4-one 2,2-dioxide has to be liberated by hydrolysis is formed in the cyclization reaction. Hydrolysis is carried out by adding water or ice, appropriately in a molar amount of about 2-fold to 6-fold—in relation to the excess of $SO_3$ used.

A 2- phase or (if 6-methyl-3,4-dihydro-1,2,3-oxathiazin-4-one 2,2-dioxide has already been precipitated) 3-phase mixture is then present after the hydrolysis. The bulk of the 6-methyl-3,4-dihydro-1,2,3-oxathiazin-4-one 2,2-dioxide present is dissolved in the organic phase and the sulfuric acid phase. The organic phase is then separated off.

The aqueous sulfuric acid phase—together with any 6-methyl-3,4-dihydro-1,2,3-oxathiazin-4-one 2,2-dioxide which has precipitated—is preferably also extracted with a water-immiscible, inert organic solvent—in particular the same solvent in which the cyclization reaction has also been carried out—and the extract is combined with the organic phase previously separated off.

If the inert organic solvent used for the cyclization reaction has already been removed, for example by evaporation in accordance with the "short-time variant" of patent application No. P 3,527,050.5 (HOE 85/F 134), the 6-methyl-3,4-dihydro-1,2,3-oxathiazin-4-one 2,2-dioxide present is mainly dissolved only in the sulfuric acid phase. In this case, for the working up procedure according to the invention, the 6-methyl-3,4-dihydro-1,2,3-oxathiazin-4-one 2,2-dioxide would have to be extracted again as completely as possible by means of an inert organic solvent of the type previously described.

The organic phase which has been separated off from the aqueous sulfuric acid phase, or the corresponding combined organic phases, are then purified by extraction with a fairly small volume of water or dilute aqueous sulfuric acid; purification only by means of water is preferred. If dilute aqueous sulfuric acid is used for the purification, its concentration is preferably between about 2 and 20%.

The ratio by volume of the organic phase to the aqueous or aqueous sulfuric acid extraction phase is generally about (20–5):1. However, effective purification can often still be achieved even with substantially smaller amounts of water.

In the simplest case, extraction is effected by stirring the two phases in a stirred flask or a stirred kettle; in principle, suitable special devices are all types of industrial extraction equipment, such as, for example, mixer-settler equipment, sieve-plate columns, packed columns, Karr columns etc. Mixing units, such as, for example, static mixers, can also be used in order to intensify the contact between the extraction phases.

The extraction can be carried out either discontinuously or continuously.

In general, depending on the amount of water employed, the proportion of 6-methyl-3,4-dihydro-1,2,3-oxathiazin-4-one 2,2-dioxide extracted is between about 2 and 30% by weight. It is important for the economic operation of the whole process to recycle the water phase (together with the relatively small amounts of extracted 6-methyl-3,4-dihydro-1,2,3-oxathiazin-4-one 2,2-dioxide) to the hydrolysis of the "$SO_3$-adduct". This can be carried out either batchwise or continuously.

The non-toxic salts of 6-methyl-3,4-dihydro-1,2,3-oxathiazin-4-one 2,2-dioxide are obtained from the purified organic phase or the purified combined organic phases by neutralization with bases. Bases suitable for this purpose are those containing non-toxic cations. Potassium bases (solutions of KOH, $KHCO_3$, $K_2CO_3$ etc.) are preferred, in particular KOH.

The neutralization of the 6-methyl-3,4-dihydro-1,2,3-oxathiazin-4-one 2,2-dioxide and the isolation of non-toxic salts thereof from the purified organic phase containing the 6-methyl-3,4-dihydro-1,2,3-oxathiazin-4-one 2,2-dioxide are advantageously effected, for example, by evaporating the organic phase, taking up the residue in water or a lower aliphatic alcohol, neutralizing the solution with an aqueous or aqueous alcoholic base and crystallizing from this solution, or, for instance, also by effecting intensive contact between the purified organic phase, or the corresponding combined organic phases, and aqueous alkali solution. The intensive contact is generally effected in the manner of an extraction, using the processes customary for this purpose, in the customary devices such as have already been described above. Mixing units, such as, for example, static mixers, can also be used for this purpose.

In general, sufficient base is added in the neutralization for the pH of the aqueous alcoholic phase, or of the purely aqueous phase, to reach a value of about 5 to 12, preferably about 8 to 11. The 6-methyl-3,4-dihydro-1,2,3-oxathiazin-4-one 2,2-dioxide salt is then isolated in a customary manner (by crystallization) from the aqueous alcoholic phase or the purely aqueous phase.

If, for example, dilute aqueous KOH of a concentration between about 1 and 10%, preferably about 4 to 8%, is used for the neutralization when intensive contact is effected between the purified organic phases and aqueous bases, the salt is isolated by separating off the aqueous phase and then concentrating and cooling it, whereupon crystalline acesulfam K is precipitated having a purity, after drying, of normally over 99.5%. The remainder (approx. 0.5%) is potassium sulphate.

If the neutralization is carried out with more concentrated aqueous KOH—i.e. potassium hydroxide solution having a concentration between about 10 and 50%, preferably between about 20 and 35%—part of the acesulfam K formed crystallizes out immediately, without further treatment, during the intensive contact between the potassium hydroxide solution and the appropriate purified organic phase. This product also has a degree of purity which is normally over 99.5%. The remainder of the acesulfam K is obtained by concentrating and, if necessary, cooling the aqueous solution.

It is advantageous to carry out the two neutralization stages described above in such a way that the intensive contact between the aqueous base and the organic phase is effected very rapidly—preferably within times from about 1 second to 60 seconds, in particular about 2 to 10 seconds. This has the effect of increasing the space-time yield of this stage. Examples of devices suitable for this purpose are thin film reactors, falling film reactors or mixing units.

A further preferred embodiment of the neutralization of the 6-methyl-3,4-dihydro-1,2,3-oxathiazin-4-one 2,2-dioxide consists in evaporating the organic solvent from the (purified) organic phase containing this compound while simultaneously adding water, and neutralizing the aqueous solution of 6-methyl-3,4-dihydro-1,2,3-oxathiazin-4-one 2,2-dioxide thus obtained with a base, preferably with a potassium base and especially with KOH. However, this embodiment only works successfully if the organic phase involved contains solvents having boiling points below 100° C. (under normal pressure), since otherwise the water metered in would also immediately evaporate with the solvent. Preferred devices for this embodiment are appliances for rapid evaporation, such as, for example, thin film evaporators or falling film evaporators.

A further preferred embodiment of the invention consists in neutralizing the 6-methyl-3,4-dihydro-1,2,3-oxathiazin-4-one 2,2-dioxide by evaporating the organic solvent from the (purified) organic phase containing this compound while simultaneously adding an aqueous base, preferably an aqueous potassium base and especially aqueous KOH. This embodiment also only works successfully if the organic solvents have boiling points below 100° C. (under normal pressure). Preferred devices for this embodiment are also appliances for rapid evaporation, such as, for example, thin film evaporators or falling film evaporators. The resulting product in this case is a heated aqueous solution from which the 6-methyl-3,4-dihydro-1,2,3-oxathiazin-4-one 2,2-dioxide salt crystallizes out when the solution is cooled and, if necessary, evaporated.

Yields (=extent of isolation) of in all cases about 80–90%, relative to the 6-methyl-3,4-dihydro-1,2,3-oxathiazin-4-one 2,2-dioxide present in the organic phase before neutralization can be achieved in all the above embodiments of the neutralization process. If desired, the yield can be increased further by additionally evaporating the aqueous phases obtained after the removal of the acesulfam K. Relative to the acetoacetamid-N-sulfonic acid or acetoacetamide-N-sulfonates, the yields are lower by the factor of the yield in the reaction.

To meet demands for extreme purity it is also possible additionally to recrystallize the acesulfam K from water, if necessary in the presence of active charcoal.

The examples which follow are intended to illustrate the invention further. In the examples 6-methyl-3,4-dihydro-1,2,3-oxathiazin-4-one 2,2-dioxide is abbreviated to "ASH" and its potassium salt to "ASK".

Preparation of the acetoacetamide-N-sulfonate starting material used for the examples 97.1 g (1.0 mol) of sulfamic acid were suspended in 1.0 of methylene chloride. 106 g (1.05 mol) of triethylamine were added with stirring, whereupon the sulfamic acid dissolved in the form of its triethylammonium salt. After 6 g (0.1 mol) of glacial acetic acid had been added, 93.8 g (1.08 mol) of 97% strength diketene were added dropwise in the course of 1 hour, with stirring, at an internal temperature of 15° C. As determined by HPLC (=high pressure liquid chromatography) analysis, the yield of acetoacetamide-N-sulfonate was 90%. The solution thus obtained was used directly for further reaction.

EXAMPLE 1

Cyclization and hydrolysis 400 ml of a 15% strength solution of $SO_3$ in $CH_2Cl_2$ were initially placed in a round-bottomed flask, blanketed with nitrogen. 1850 ml of the (15% strength) $SO_3/CH_2Cl_2$ solution and, simultaneously, the solution of acetoacetamide-N-sulfonate in $CH_2Cl_2$ described above were added dropwise in the course of 25 minutes, with stirring, at an internal temperature of −30° C. (isopropanol/solid carbon dioxide cooling: −40° to −50° C.).

Hydrolysis was effected by adding 500 ml of water dropwise, in the course of approx. 30 minutes, starting at −30° C., with vigorous external cooling. In the course of this the temperature rose rapidly from −30° C. to 0° C.; later it was kept at 0° to +5° C.

Preparation of an ASH/methylene chloride solution

The organic phase was separated off at 5° C., and the aqueous sulfuric acid phase was extracted again with twice 1.0 of $CH_2Cl_2$. This gave a solution of 132 g of ASH in 5.0 of methylene chloride (=1.9% strength solution). Yield: 81% (relative to sulfamic acid).

The isolation of ASK 2.5 of this ASH/methylene chloride solution were stirred with 250 ml of water for 2 hours. The organic phase was then evaporated in vacuo. The residue was dissolved in its own weight of methanol, and the pH was then adjusted to 8–10 with 20% strength KOH/methanol (=KOH/methanol precipitation). After being filtered off and dried, 69.5 g of ASK were isolated (yield: 85%, relative to 66 g of ASH employed).

| Analysis: | |
|---|---|
| ASK | $K_2SO_4$ |
| 99.6% | 0.4% |

Comparison 2.5 of the 1.9% strength ASH/methylene chloride solution prepared as described above were evaporated in vacuo without further purification operations. The residue was then dissolved in its own weight of methanol and the pH was then adjusted to 8 to 10 with 20% strength KOH/methanol. After being filtered off and dried, 96.5 g of crude ASK were isolated (yield: 98%, relative to 66 g of ASH employed); the composition of this was 83% of ASK, together with a $K_2SO_4$ content of 8.8% (relative to ASK).

EXAMPLE 2

Recycling to the hydrolysis stage the aqueous phase obtained when the organic ASH phase was extracted with water.

In each case 1/10 of the amount of starting materials described in Example 1 was employed for the cyclization reaction. The ASH/methylene chloride solution obtained (500 ml) was then stirred in each case with 50 ml of water for 2 hours. The water phase thus obtained was then employed for the hydrolysis in the next experiment.

The ASK samples listed in Table 1 were isolated by KOH/methanol precipitation (see Example 1) after 10 experiments with the water phase recycled 9 times.

TABLE 1

| Experiment No. | ASK (g) | Analysis | |
|---|---|---|---|
| | | ASK (%) | $K_2SO_4$ (%) |
| 1 | 13.8 | 99.9 | 0.3 |
| 2 | 15.7 | 99.5 | 0.4 |
| 3 | 16.0 | 99.5 | 0.5 |
| 4 | 16.4 | 99.7 | 0.3 |
| 5 | 16.2 | 99.9 | 0.2 |
| 6 | 15.9 | 100.0 | 0.2 |
| 7 | 16.5 | 99.8 | 0.3 |
| 8 | 16.2 | 99.6 | 0.4 |
| 9 | 16.3 | 99.6 | 0.5 |
| 10 | 16.0 | 99.9 | 0.2 |

EXAMPLE 3

Extractive neutralization of the ASH/methylene chloride phase with 7% strength potassium hydroxide solution.

5.0 l of the 1.9% strength ASH/methylene chloride solution prepared in accordance with Example 1 were stirred with 500 ml of water for 2 hours. The organic phase (containing 112 g of ASH) was separated off and stirred with 600 g of 7% strength potassium hydroxide solution for 1.5 hours. The aqueous phase was then separated off. 490 g of water were removed from this solution by vacuum (60 mbar) distillation. 115.7 g of ASK were isolated after the residue had been cooled to 0° C. and the product filtered off and dried.

Yield: 84% (relative to 112 g of ASH).

| Analysis: | |
|---|---|
| ASK | $K_2SO_4$ |
| 99.9% | 0.05% |

A further 13.0 g of ASK were isolated after further evaporation of the crystallization mother liquor.

Yield: 9% (relative to 112 g of ASH).

| Analysis: | |
|---|---|
| ASK | $K_2SO_4$ |
| 99.8% | 0.3% |

EXAMPLE 4

Extractive neutralization of the ASH/methylene chloride phase with 30% strength potassium hydroxide solution in a stirred flask.

5.0 l of the ASH/methylene chloride solution prepared in accordance with Example 1 were stirred with 500 ml of water for 2 hours. The organic phase (=112 g of ASH) was separated off and stirred with 144.0 g of 30% strength KOH for 0.5 hour. The reaction mixture was then filtered. 112.8 g of ASK were obtained after drying.

Yield: 81.5% (relative to 112 g of ASH).

| Analysis: | |
|---|---|
| ASK | $K_2SO_4$ |
| 99.8% | 0.1% |

EXAMPLE 5

Extractive neutralization of the ASH/methylene chloride phase with 30% strength potassium hydroxide solution in a thin film reactor.

The apparatus comprised a commercially available laboratory thin film evaporator having an effective length of 22 cm and an effective surface area of 160 cm², which was operated as a thin film reactor. 2.5 l of the ASH/methylene chloride solution, treated with water as in Example 4, and 65.4 g of 30% strength KOH were pumped in simultaneously in the course of 1 hour (rotor speed approx. 800 r.p.m.). The ASK formed was filtered off continuously by means of a suction filter from the reaction mixture leaving the reactor. After drying 56.1 g of ASK were obtained.

Yield: 81% (relative to 56 g of ASH).

| Analysis: | |
|---|---|
| ASK | $K_2SO_4$ |
| 99.7% | 0.3% |

As calculated from the dead space in the reactor and the volume flows of the products fed in, the average dwell time was 2.5 seconds.

EXAMPLE 6

Removal of the $CH_2Cl_2$ by distillation, with the addition of water, in a thin film evaporator.

The apparatus comprised a commercially available laboratory thin film evaporator having an effective length of 22 cm and an effective surface area of 160 cm².

5.0 l/hour of an ASH/CH$_2$Cl$_2$ solution (112 g of ASH), treated with 500 ml of water as in Example 3, and 180 g/hour of water were allowed to flow simultaneously into the evaporator, the temperature of the heating jacket being 115° C. After cooling to room temperature, the approx. 60% strength ASH/water solution leaving the evaporator was neutralized, with stirring, with 78.5 g of 50% strength potassium hydroxide solution. 110.7 g of ASK were isolated after the mixture had been cooled to 0° C.

Yield: 80% (relative to 112 g of ASH).

| Analysis: | |
|---|---|
| ASK | K$_2$SO$_4$ |
| 99.9% | 0.2% |

A further 12.0 g of ASK were isolated after the crystallization mother liquor had been evaporated further.

Yield: 9% (relative to 112 g of ASH).

| Analysis: | |
|---|---|
| ASK | K$_2$SO$_4$ |
| 99.7% | 0.3% |

EXAMPLE 7

Removing the CH$_2$Cl$_2$ by distillation, with the addition of potassium hydroxide solution, in a thin film evaporator.

5.0 /hour of the same ASH/CH$_2$Cl$_2$ solution as in Example 6 and 250 g of 16% strength potassium hydroxide solution were fed simultaneously into the same apparatus as in Example 6, with the heating medium at a temperature of 115° C. A homogeneous aqueous solution of ASK flowed out of the evaporator (T=105° C.). After this solution had been cooled to 0° C. the ASK which had crystallized out was filtered off and dried in vacuo.

Yield: 127.2 g (92%) (relative to 112 g of ASH).

| Analysis: | |
|---|---|
| ASK | K$_2$SO$_4$ |
| 99.9% | 0.1% |

We claim:

1. A process for purifying an organic phase obtained from the synthesis of the cyclic dioxide 6-methyl-3,4-dihydro-1,2,3-oxathiazin-4-one 2,2,-dioxide, said organic phase comprising said dioxide dissolved in a substantially water-immiscible, inert organic solvent, comprising the steps of:
purifying said organic phase by extraction with an aqueous medium, neutralizing the said dioxide with a base which forms non-toxic salts, and isolating said dioxide in the form of the resulting non-toxic salt thereof.

2. A process as claimed in claim 1, wherein the substantially water-immiscible, inert organic solvent comprises an aliphatic chlorinated hydrocarbon.

3. A process as claimed in claim 1, wherein said organic phase is obtained by dissolving acetoacetamide-N-sulfonic acid, or a salt thereof, in an aliphatic chlorinated hydrocarbon solvent, cyclizing the acetoacetamide-N-sulfonic acid or salt with SO$_3$, the SO$_3$ being dissolved in said solvent, thereby obtaining either said dioxide dissolved in said solvent or the SO$_3$-adduct of said dioxide, dissolved in said solvent.

4. A process as claimed in claim 3, wherein more than a molar amount of SO$_3$ is added to each mole of acetoacetamide-N-sulfonic acid or salt thereof, so that the said SO$_3$-adduct will be formed.

5. The process as claimed in claim 4, wherein the said SO$_3$-adduct is hydrolyzed to recover said dioxide.

6. The process as claimed in claim 5, wherein the aqueous sulfuric acid phase formed during the hydrolysis of said SO$_3$-adduct, together with any said dioxide which may have precipitated, is again extracted with a water-immiscible inert organic solvent, and the organic extract is combined with the organic phase which separated out in the hydrolysis.

7. A process as claimed in claim 1, wherein said aqueous medium used in the purification step is water or dilute sulfuric acid.

8. A process as claimed in claim 7, wherein more than a molar amount of SO$_3$ is added to each mole of acetoacetamide-N-sulfonic acid or salt thereof, so that the SO$_3$-adduct of said dioxide is formed; said dioxide is recovered from the SO$_3$-adduct by hydrolysis; and the aqueous medium used in the purification step is recycled for use in said hydrolysis.

9. A process as claimed in claim 1, wherein the isolation of said dioxide in the form of the resulting non-toxic salt thereof is effected by evaporating said organic phase and neutralizing the resulting residue with a base.

10. A process as claimed in claim 9, wherein said base is a potassium hydroxide solution.

11. A process as claimed in claim 1, wherein the isolation of said dioxide in the form of the non-toxic salt thereof is effected by intensively contacting the purified organic phase containing said dioxide with an aqueous solution of a base.

12. A process as claimed in claim 1, wherein the isolation of said dioxide in the form of the non-toxic salt thereof is effected by evaporating off said solvent from the purified organic phase, with simultaneous addition of water or an aqueous solution containing a base.

13. A process as claimed in claim 12, wherein said solvent is evaporated off with simultaneous addition of water, and the resulting aqueous solution of said dioxide is neutralized with a base.

14. A process as claimed in claim 12, wherein the evaporation of said solvent with simultaneous addition of water or a said aqueous solution is carried out in a thin film evaporator or a falling film evaporator.

* * * * *